(12) United States Patent
Reich

(10) Patent No.: US 11,666,442 B2
(45) Date of Patent: Jun. 6, 2023

(54) TECHNIQUES FOR FACILITATING HEART VALVE TETHERING AND CHORD REPLACEMENT

(71) Applicant: Edwards Lifesciences Innovation (Israel) Ltd., Caesarea (IL)

(72) Inventor: Tal Reich, Moledet (IL)

(73) Assignee: Edwards Lifesciences Innovation (Israel) Ltd., Caesarea (IL)

(*) Notice: Subject to any disclaimer, the term of this patent is extended or adjusted under 35 U.S.C. 154(b) by 371 days.

(21) Appl. No.: 16/926,580

(22) Filed: Jul. 10, 2020

(65) Prior Publication Data

US 2020/0337840 A1 Oct. 29, 2020

Related U.S. Application Data

(63) Continuation of application No. PCT/IL2019/050083, filed on Jan. 22, 2019.

(60) Provisional application No. 62/622,315, filed on Jan. 26, 2018.

(51) Int. Cl.
*A61F 2/24* (2006.01)

(52) U.S. Cl.
CPC .......... *A61F 2/2457* (2013.01); *A61F 2/2466* (2013.01); *A61F 2220/0016* (2013.01); *A61F 2250/0098* (2013.01)

(58) Field of Classification Search
None
See application file for complete search history.

(56) References Cited

U.S. PATENT DOCUMENTS

| | | | |
|---|---|---|---|
| 3,604,488 A | 9/1971 | Wishart et al. |
| 3,656,185 A | 4/1972 | Carpentier |
| 3,840,018 A | 10/1974 | Heifetz |
| 3,881,366 A | 5/1975 | Bradley et al. |
| 3,898,701 A | 8/1975 | La Russa |

(Continued)

FOREIGN PATENT DOCUMENTS

| | | |
|---|---|---|
| CN | 113331995 A | 9/2021 |
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Suba Ganesan
(74) *Attorney, Agent, or Firm* — Thomas C. Richardson

(57) ABSTRACT

A method is described, for use with a native valve of a heart of a subject, the valve being disposed between an atrium and a ventricle of the heart. A first radiopaque marker and a second radiopaque marker are percutaneously advanced to the heart. The first radiopaque marker is placed against a tissue site in the ventricle. The second radiopaque marker is placed against a leaflet of the valve. A distance is measured between the first radiopaque marker at the tissue site, and the second radiopaque marker at the leaflet. Responsively to the measured distance, a chord-length is determined. An artificial chord, selected based on the chord-length, is implanted in the heart. Other embodiments are also described.

22 Claims, 8 Drawing Sheets

(56) References Cited

U.S. PATENT DOCUMENTS

| | | |
|---|---|---|
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,860,923 A | 1/1999 | Lenker et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |

(56) References Cited

U.S. PATENT DOCUMENTS

| | | |
|---|---|---|
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |

(56) References Cited

U.S. PATENT DOCUMENTS

| | | |
|---|---|---|
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Miio |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |

(56) References Cited

U.S. PATENT DOCUMENTS

| | | |
|---|---|---|
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stabler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |

(56) References Cited

U.S. PATENT DOCUMENTS

| | | |
|---|---|---|
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |

(56) References Cited

U.S. PATENT DOCUMENTS

| | | |
|---|---|---|
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0085577 A1* | 3/2020 | Vola ............ A61F 2/2457 |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2022/0096232 A1 | 3/2022 | Skaro et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |

OTHER PUBLICATIONS

Ahmadi, A., G. Spillner, and Th Johannessen. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneousiy adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgicai Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

(56) References Cited

OTHER PUBLICATIONS

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneousiy adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

TECHNIQUES FOR FACILITATING HEART VALVE TETHERING AND CHORD REPLACEMENT

CROSS-REFERENCES TO RELATED APPLICATIONS

The present application is a continuation from Patent Cooperation Treaty Application No. PCT/IL2019/050083 to Reich, filed on Jan. 22, 2019, published as WO 2019/145941, which claims priority from U.S. Provisional Patent Application 62/622,315 to Reich, filed Jan. 26, 2018, each of which is incorporated herein by reference.

FIELD OF THE INVENTION

Some applications of the present invention relate in general to cardiac repair. More specifically, some applications of the present invention relate to facilitating implantation of artificial chordae tendineae.

BACKGROUND

Ischemic heart disease can cause mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve can prevent the valve leaflets from fully coapting when the valve is closed. Mitral regurgitation of blood from the left ventricle into the left atrium can result in increased total stroke volume and decreased cardiac output, and ultimate weakening of the left ventricle secondary to a volume overload and a pressure overload of the left atrium.

Chronic or acute left ventricular dilatation can lead to papillary muscle displacement with increased leaflet tethering due to tension on chordae tendineae, as well as annular dilatation.

SUMMARY OF THE INVENTION

Techniques are provided for determining an appropriate chord-length for an artificial chorda tendinea by placing markers, such as radiopaque markers, against tissue sites within the heart, and calculating (e.g., measuring, calculating using a computer program, etc.) a distance between the markers. Typically, one marker is placed against a papillary muscle, and another marker is placed against one or more leaflets, and the chord-length is based on the calculated or measured distance between these markers. The artificial chorda tendinea can then be implanted.

The determination of the chord-length and the implantation of the artificial chorda tendinea are typically performed percutaneously, e.g., transluminally (i.e., via a blood vessel), such as transfemorally, transseptally, etc. Therefore, the techniques described herein can be performed without line-of-sight or direct visualization, but instead can be facilitated by imaging technologies such as echocardiography and fluoroscopy.

There is therefore provided, in an exemplary application, a method for use in a heart (e.g., for use with a native valve of a heart of a subject). The method includes percutaneously advancing a first radiopaque marker and a second radiopaque marker to the heart. The method also includes placing the first radiopaque marker against a first tissue site in the heart (e.g., the ventricle) and placing the second radiopaque marker at a second tissue site in the heart (e.g., at or proximate a valve of the heart, such as an atrioventricular valve, etc.). The method also includes calculating and/or measuring a distance between the first radiopaque marker at the first tissue site, and the second radiopaque marker at the second tissue site, and responsively to the distance (i.e., the distance calculated or measured), determining a tether-length.

Placing the second radiopaque marker against the leaflet can include placing the second radiopaque marker against a free edge of the leaflet. Placing the first radiopaque marker against the first tissue site can include anchoring, to the first tissue site, an anchor that includes the first radiopaque marker. Placing the first radiopaque marker against the first tissue site can include placing the first radiopaque marker against the first tissue site under echocardiographic guidance. Placing the second radiopaque marker against the second tissue site can include placing the second radiopaque marker against the second tissue site under echocardiographic guidance.

Calculating or measuring the distance can include measuring the distance using fluoroscopy and/or on a fluoroscopic image. Calculating or measuring the distance can include using a computer program or software to measure and/or estimate the distance between markers. The computer program or software can use image recognition and/or other tools, sensors, inputs, etc. to measure and/or estimate the distance between markers.

Advancing the first and second radiopaque markers can include advancing the first and second radiopaque markers transluminally (e.g., transfemorally, transseptally, etc.).

The second tissue site can be a first leaflet of a valve of the heart, and placing the first radiopaque marker against the second tissue site can include placing the first radiopaque marker at a systolic coaptation level between the first leaflet and a second leaflet of the valve.

The first tissue site can be on a papillary muscle, and placing the first radiopaque marker against the first tissue site can include placing the first radiopaque marker against the papillary muscle.

The method can further include selecting the tether based on and/or having the tether-length from a selection of tethers that includes at least one tether that does not have the tether-length (e.g., being longer than the tether-length). The method can include adjusting the tether to the tether-length. For example, the method can include trimming the tether to the tether-length.

The method can further include implanting, in the heart, a tether selected based on and/or having the tether-length.

Implanting the tether can include attaching a first end portion of the tether to the tissue site and attaching a second end portion of the tether to the second tissue site.

The method can also include additional steps described elsewhere in this disclosure.

In an exemplary application, a method for use with a native valve of a heart of a subject (the valve can be disposed between an atrium and a ventricle of the heart) the method including:

percutaneously advancing a first radiopaque marker and a second radiopaque marker to the heart;

placing the first radiopaque marker against a tissue site in the ventricle;

placing the second radiopaque marker against a leaflet of the valve;

calculating or measuring a distance between the first radiopaque marker at the tissue site, and the second radiopaque marker at the leaflet; and responsively to the distance (i.e., the calculated or measured distance), determining a chord-length.

In an application, placing the first radiopaque marker against the tissue site includes anchoring, to the tissue site, a tissue anchor that includes the first radiopaque marker.

In an application, placing the first radiopaque marker against the tissue site includes placing the first radiopaque marker against the tissue site under echocardiographic guidance.

In an application, placing the second radiopaque marker against the leaflet includes placing the first radiopaque marker against the leaflet under echocardiographic guidance.

In an application, calculating or measuring the distance includes measuring the distance using fluoroscopy and/or measuring the distance on a fluoroscopic image. Calculating or measuring the distance can include using a computer program or software to measure and/or estimate the distance between markers. The computer program or software can use image recognition and/or other tools, sensors, inputs, etc. to measure and/or estimate the distance between markers.

In an application, advancing the first and second radiopaque markers includes advancing the first and second radiopaque markers transluminally.

In an application, the leaflet is a first leaflet, and placing the first radiopaque marker against the leaflet includes placing the first radiopaque marker at a systolic coaptation level between the first leaflet and a second leaflet of the valve.

In an application, the tissue site is on a papillary muscle, and placing the first radiopaque marker against the tissue site includes placing the first radiopaque marker against the papillary muscle.

In an application, the method further includes selecting the artificial chord based on and/or having the chord-length from a selection of chords that includes at least one chord that does not have the chord-length.

In an application, the method further includes adjusting the artificial chord to the chord-length.

In an application, the method further includes trimming the artificial chord to the chord-length.

The method can further include implanting, in the heart, an artificial chord based on and/or having the chord-length.

In an application, implanting the artificial chord includes attaching a first end portion of the artificial chord to the tissue site and attaching a second end portion of the artificial chord to the leaflet.

In an application:

the leaflet is a first leaflet, the artificial chord is a first artificial chord, implanting the artificial chord includes attaching a first end portion of the first artificial chord to the tissue site and attaching a second end portion of the first artificial chord to the leaflet, and the method further includes implanting a second artificial chord by attaching a second end portion of the second artificial chord to a second leaflet of the native valve.

In an application, implanting the second artificial chord includes attaching a first end portion of the second artificial chord to a second tissue site in the ventricle.

In an application, the first radiopaque marker is disposed on a first elongate tool, and placing the first radiopaque marker against the tissue site includes placing the first tool against the tissue site.

In an application, the first tool is shaped to define a lumen therethrough, and the method further includes advancing the artificial chord to the heart within the lumen.

In an application, implanting the artificial chord includes anchoring a first end portion of the artificial chord to the tissue site without removing the first tool from the tissue site.

In an application, implanting the artificial chord includes anchoring a tissue anchor to the tissue site without removing the first tool from the tissue site.

In an application, a first end portion of the artificial chord is attached to the tissue anchor, and anchoring the tissue anchor to the tissue site includes anchoring the first end portion of the artificial chord to the tissue site.

In an application, an elongate guide member is coupled to the tissue anchor, and anchoring the tissue anchor to the tissue site includes anchoring the guide member to the tissue site.

In an application, implanting the artificial chord includes, subsequently to anchoring the tissue anchor, advancing the artificial chord along the guide member to the tissue anchor and coupling the artificial chord to the tissue anchor.

In an application, the method further includes, subsequently to anchoring the tissue anchor, removing the first tool from the tissue site and the tissue anchor, and advancing the artificial chord along the guide member to the tissue anchor includes advancing the artificial chord along the guide member to the tissue anchor subsequently to removing the first tool from the tissue site and the tissue anchor.

In an application, the method further includes, subsequently to coupling the artificial chord to the tissue anchor, decoupling the guide member from the tissue anchor.

In an application, the first radiopaque marker is disposed on a distal end of the first tool, and placing the first radiopaque marker against the tissue site includes placing the distal end of the first tool against the tissue site.

In an application, the first radiopaque marker is disposed on a first elongate tool, the second radiopaque marker is disposed on a second elongate tool that is slidably coupled to the first tool, and:

advancing the first radiopaque marker and the second radiopaque marker to the heart includes advancing the first tool and the second tool to the heart, and the method further includes sliding the second tool with respect to the first tool in order to place at least one radiopaque marker selected from the group consisting of: the first radiopaque marker and the second radiopaque marker.

In an application:

the second tool includes a longitudinal shaft and an appendage, the second radiopaque marker is disposed on the appendage, the method further includes extending the appendage laterally from the longitudinal shaft, and placing the second radiopaque marker against the leaflet includes moving the second tool until the appendage abuts the leaflet.

In an application, the first tool is slidable within the second tool, and sliding the second tool with respect to the first tool includes sliding the first tool within the second tool.

There is further provided, in an exemplary application, a method, including:

advancing a first marker (e.g., a first radiopaque marker) and a second marker (e.g., a second radiopaque marker)

along a simulated vasculature to a simulated heart, the heart having a simulated valve disposed between a simulated atrium and a simulated ventricle;

placing the first marker against a simulated tissue site in the ventricle;

placing the second marker against a simulated leaflet of the valve;

calculating or measuring a distance between the first marker at the tissue site, and the second marker at the leaflet; and responsively to the distance, determining a chord-length.

The simulated vasculature can be a computer-simulated vasculature, the simulated heart can be a computer-simulated heart, and the step of advancing can include advancing the first marker and the second marker along the computer-simulated vasculature to the computer-simulated heart.

The simulated vasculature can be a physical model of vasculature, the simulated heart can be a physical model of a heart, and the step of advancing can include advancing the first marker and the second marker along the physical model of the vasculature to the physical model of the heart.

The markers can be radiopaque markers, computer-simulated markers, or computer-simulated radiopaque markers.

In an application, calculating or measuring the distance includes measuring the distance using fluoroscopy and/or measuring the distance on a fluoroscopic image. Calculating or measuring the distance can include using a computer program or software to measure and/or estimate the distance between markers. The computer program or software can use image recognition and/or other tools, sensors, inputs, etc. to measure and/or estimate the distance between markers.

In some applications, the first marker is a first computer-simulated radiopaque marker and the second marker is a second computer-simulated radiopaque marker, and calculating the distance comprises measuring the distance between the first computer-simulated radiopaque marker and the second computer-simulated radiopaque marker on a computer-simulated fluoroscopic image.

The simulated heart can be a simulation of a heart of a particular human subject, and the method can be a method for planning a chord-implantation procedure on the particular human subject.

In an application, placing the first marker against the tissue site includes anchoring, to the tissue site, a tissue anchor that includes the first marker.

In an application, placing the first marker against the tissue site includes placing the first marker against the tissue site under echocardiographic guidance.

In an application, placing the second marker against the leaflet includes placing the first marker against the leaflet under echocardiographic guidance.

The echocardiographic guidance can use actual ultrasound, or can be computer-simulated.

In an application, calculating or measuring the distance includes measuring the distance using fluoroscopy.

The fluoroscopy can be actual fluoroscopy, or can be computer-simulated fluoroscopy.

In an application, the leaflet is a first simulated leaflet, and placing the first marker against the leaflet includes placing the first marker at a coaptation level between the first leaflet and a second simulated leaflet of the valve.

In an application, the tissue site is on a simulated papillary muscle, and placing the first marker against the tissue site includes placing the first marker against the papillary muscle.

In an application, the method further includes selecting the artificial chord based on the chord-length from a selection of chords that includes at least one chord that does not have the chord-length.

In an application, the method further includes adjusting the artificial chord to the chord-length.

In an application, the method further includes trimming the artificial chord to the chord-length.

In an application, the method further includes implanting, in the heart, an artificial chord selected based on the chord-length.

In an application, implanting the artificial chord includes attaching a first end portion of the artificial chord to the tissue site and attaching a second end portion of the artificial chord to the leaflet.

In an application:

the leaflet is a first simulated leaflet, the artificial chord is a first artificial chord, implanting the artificial chord includes attaching a first end portion of the first artificial chord to the tissue site and attaching a second end portion of the first artificial chord to the first simulated leaflet, and the method further includes implanting a second artificial chord by attaching a second end portion of the second artificial chord to a second simulated leaflet of the simulated valve.

In an application, implanting the second artificial chord includes attaching a first end portion of the second artificial chord to a second simulated tissue site in the ventricle.

In an application, the first marker is disposed on a first elongate tool, and placing the first marker against the tissue site includes placing the first tool against the tissue site.

In an application, the first tool is shaped to define a lumen therethrough, and the method further includes advancing the artificial chord to the heart within the lumen.

In an application, implanting the artificial chord includes anchoring a first end portion of the artificial chord to the tissue site without removing the first tool from the tissue site.

In an application, implanting the artificial chord includes anchoring a tissue anchor to the tissue site without removing the first tool from the tissue site.

In an application, a first end portion of the artificial chord is attached to the tissue anchor, and anchoring the tissue anchor to the tissue site includes anchoring the first end portion of the artificial chord to the tissue site.

In an application, an elongate guide member is coupled to the tissue anchor, and anchoring the tissue anchor to the tissue site includes anchoring the guide member to the tissue site.

In an application, implanting the artificial chord includes, subsequently to anchoring the tissue anchor, advancing the artificial chord along the guide member to the tissue anchor and coupling the artificial chord to the tissue anchor.

In an application, the method further includes, subsequently to anchoring the tissue anchor, removing the first tool from the tissue site and the tissue anchor, and advancing the artificial chord along the guide member to the tissue anchor includes advancing the artificial chord along the guide member to the tissue anchor subsequently to removing the first tool from the tissue site and the tissue anchor.

In an application, the method further includes, subsequently to coupling the artificial chord to the tissue anchor, decoupling the guide member from the tissue anchor.

In an application, the first marker is disposed on a distal end of the first tool, and placing the first marker against the tissue site includes placing the distal end of the first tool against the tissue site.

In an application, the first marker is disposed on a first elongate tool, the second marker is disposed on a second elongate tool that is slidably coupled to the first tool, and:

advancing the first marker and the second marker to the heart includes advancing the first tool and the second tool to the heart, and the method further includes sliding the second tool with respect to the first tool in order to place at least one radiopaque marker selected from the group consisting of: the first marker and the second marker.

In an application:

the second tool includes a longitudinal shaft and an appendage, the second marker is disposed on the appendage, the method further includes extending the appendage laterally from the longitudinal shaft, and placing the second marker against the leaflet includes moving the second tool until the appendage abuts the leaflet.

In an application, the first tool is slidable within the second tool, and sliding the second tool with respect to the first tool includes sliding the first tool within the second tool.

There is further provided, in accordance with an application of the present invention, a method, including:

advancing a first marker (e.g., first radiopaque marker) and a second marker (e.g., second radiopaque marker) along a simulated vasculature to a simulated heart, the heart having a simulated valve disposed between a simulated atrium and a simulated ventricle;

placing the first marker against a first simulated tissue site in the ventricle;

placing the second marker at a second simulated tissue site at or proximate the valve;

calculating or measuring a distance between the first marker at the first tissue site, and the second marker at the second tissue site; and responsively to the distance, determining a tether-length.

In an application:

the simulated vasculature is a computer-simulated vasculature, and the simulated heart is a computer-simulated heart; and the step of advancing includes advancing the first marker and the second marker along the computer-simulated vasculature to the computer-simulated heart.

In an application:

the simulated vasculature is a physical model of vasculature, and the simulated heart is a physical model of a heart; and the step of advancing includes advancing the first marker and the second marker along the physical model of the vasculature to the physical model of the heart.

In an application:

the simulated heart is a simulation of a heart of a particular human subject, and the method is a method for planning a tether-implantation procedure on the particular human subject.

In an application, placing the first marker against the first tissue site includes anchoring, to the first tissue site, an anchor that includes the first marker.

In an application, placing the first marker against the first tissue site includes placing the first marker against the first tissue site under echocardiographic guidance.

In an application, placing the second marker against the second tissue site includes placing the second marker against the second tissue site under echocardiographic guidance.

In an application, calculating or measuring the distance includes measuring the distance using fluoroscopy and/or measuring the distance on a fluoroscopic image. Calculating or measuring the distance can include using a computer program or software to measure and/or estimate the distance between markers. The computer program or software can use image recognition and/or other tools, sensors, inputs, etc. to measure and/or estimate the distance between markers.

In an application, the second tissue site is a first simulated leaflet, and placing the first marker against the second tissue site includes placing the first marker at a systolic coaptation level between the first leaflet and a second simulated leaflet of the valve.

In an application, the first tissue site is on a simulated papillary muscle, and placing the first marker against the first tissue site includes placing the first marker against the papillary muscle.

In an application, the method further includes selecting the tether based on the tether-length from a selection of tethers that includes at least one tether that does not have the tether-length.

In an application, the method further includes adjusting the tether to the tether-length.

In an application, the method further includes trimming the tether to the tether-length.

In an application, the method further includes implanting, in the heart, a tether selected based on the tether-length.

In an application, implanting the tether includes attaching a first end portion of the tether to the tissue site and attaching a second end portion of the tether to the second tissue site.

The present invention will be more fully understood from the following detailed description of applications thereof, taken together with the drawings, in which:

DETAILED DESCRIPTION OF EMBODIMENTS

Figure 1A:
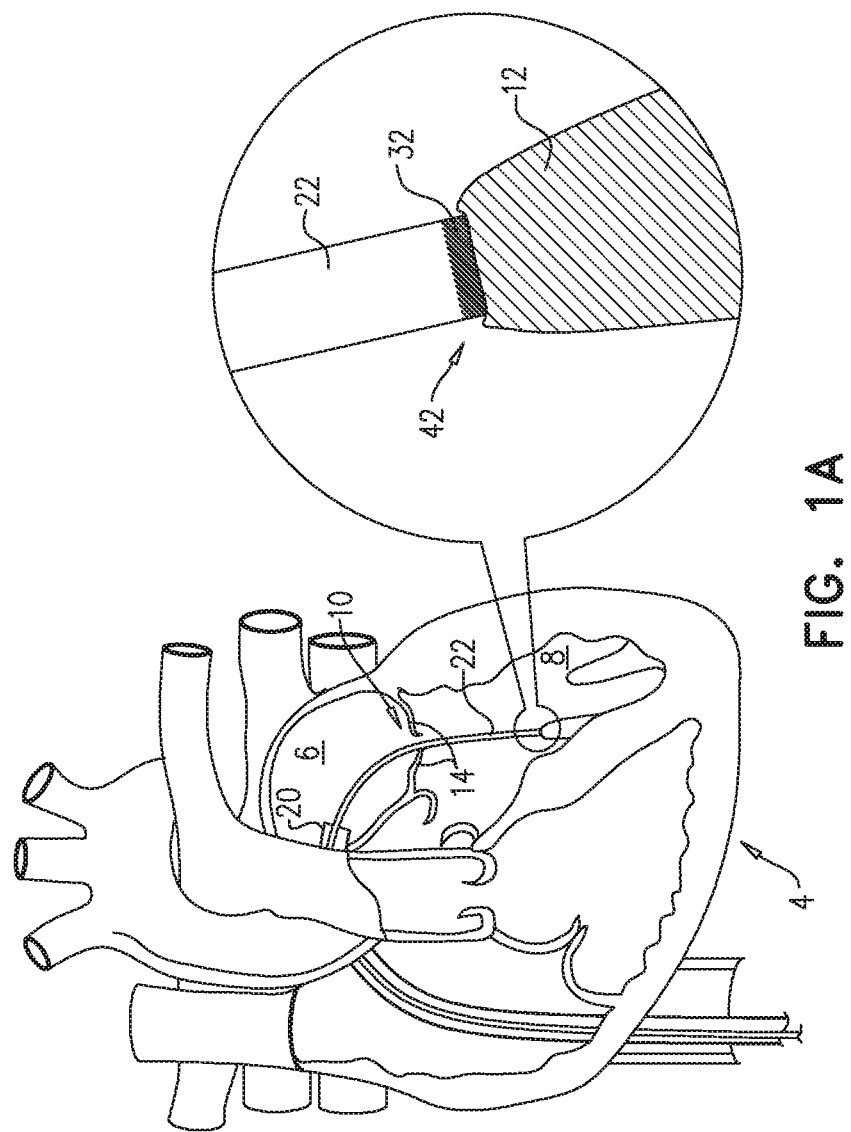
FIGS. 1A-F are schematic illustrations showing a technique for use with a native valve of a heart of a subject, in accordance with some applications of the invention.

Reference is made to FIGS. 1A-F, which are schematic illustrations showing a technique for use with a native valve 10 of a heart 4 of a subject, in accordance with some applications of the invention. Valve 10 is an atrioventricular valve, disposed between an atrium and a ventricle of the heart. For example, and as shown, valve 10 may be a mitral valve, disposed between left atrium 6 and left ventricle 8 of the heart. Valve 10 could also be a tricuspid valve. Any and all of the methods, techniques, steps, etc. described herein can be performed on a living animal or on a non-living cadaver, cadaver heart, simulator, anthropomorphic ghost, etc.

A first marker or first radiopaque marker 32 and a second marker or a second radiopaque marker 34 are advanced to the heart. Marker 32 can be disposed on (e.g., at a distal end of) a first tool 22. Marker 34 can be disposed on (e.g., at a distal end of) a second tool 24. It is to be noted that, in this context, the terms "first" and "second" are used purely to distinguish each marker from the other, and each tool from the other, and are not intended to specify an order in which these elements are arranged or used.

First marker 32 is placed against a tissue site 42 in ventricle 8 (FIG. 1A). For example, first tool 22 may be advanced into the ventricle until the distal end of the tool is disposed against tissue site 42 (e.g., a papillary muscle, heart wall, ventricular wall, septum, apex, etc.). As shown, this may be performed transluminally (e.g., transfemorally, transseptally, etc.) or transapically. In one application, a sheath 20 can be advanced transfemorally/transseptally to the heart, and tools 22 and 24 can be advanced via the sheath.

For some applications, and as shown, tissue site 42 is on a papillary muscle 12 of the heart. For some applications, tissue site 42 is on a ventricular wall (e.g., inner wall, septum, outer wall, etc.) of the heart.

Figure 1C:
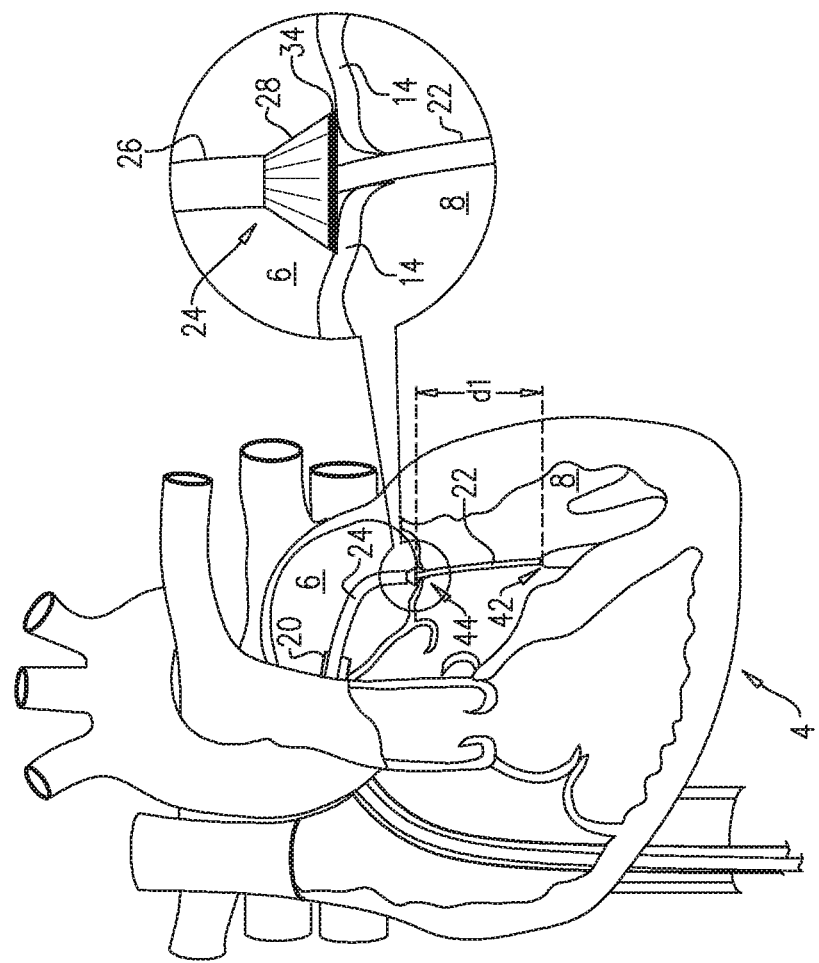
Figure 1B:
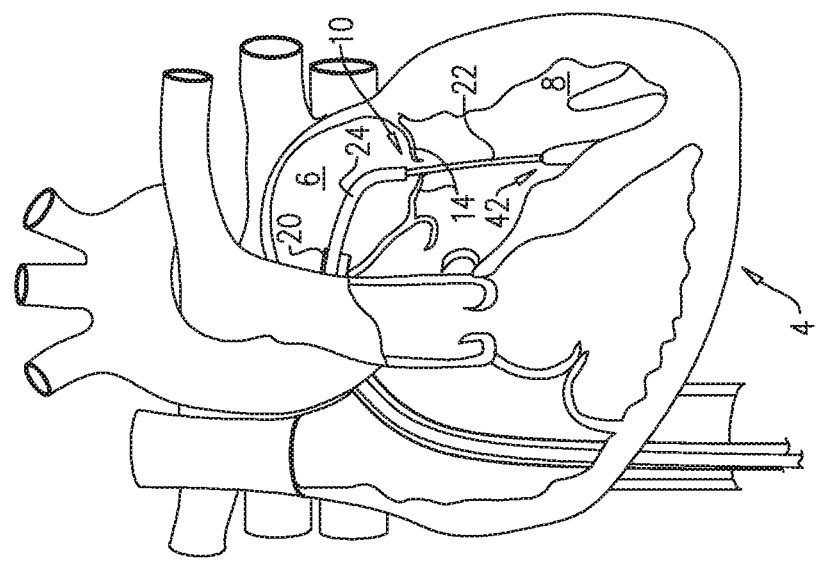

For some applications, second marker 34 is placed against a tissue site 44 in the atrium, ventricle, or between, e.g., on one or multiple leaflets 14 of valve 10 (FIGS. 1B-C). For example, second tool 24 can be advanced into the ventricle until the distal end of the tool is disposed against tissue site 44. This can be performed transluminally (e.g., transfemorally, transseptally, etc.). For some applications, marker 34 is placed against an upstream surface of leaflet 14. For some applications, marker 34 is placed at a level of systolic coaptation between two leaflets 14. For some applications, marker 34 is placed at the free edge of one or more of the leaflets. It is to be noted that the term "level of systolic coaptation" (including the specification and the claims) means the level (e.g., on the long axis of the heart) at which leaflets 14 coapt during ventricular systole. For such applications, if valve 10 suffers from leaflet flail, the level of systolic coaptation is typically the level at which the coapting regions of the leaflets coapt.

For some applications, tool 22 is slidably coupled to tool 24, the operator slides the tools with respect to each other in order to place markers 32 and 34 against their corresponding tissue sites. For example, tool 22 can be slidable within tool 24 (e.g., coaxially, as shown), or tool 24 can be slidable within tool 22. Tools 22 and 24 could also be slidable or otherwise movable adjacent to each other without necessarily being coaxial or one inside the other.

For some applications, second tool 24 includes a longitudinal shaft 26 and marker 34 is disposed on the longitudinal shaft. For some applications, and as shown in FIG. 1C, second tool 24 comprises a longitudinal shaft 26, and an appendage 28 on which marker 34 is disposed. For such applications, marker 34 is typically placed against tissue site 44, e.g., by moving tool 24 until the marker and/or appendage 28 abuts the leaflets. Appendage 28 can be laterally extendible (e.g., radially expandable) from shaft 26. For such applications, appendage 28 can be laterally extended from shaft 26 in order to provide a wide span for abutting leaflet(s) 14. For example, shaft 26 can have a lateral width of 2-10 mm, whereas appendage 28, when extended (e.g., when in an expanded state), can have a span of 6-15 mm. Alternatively or additionally, the span of appendage 28 when extended can be 0.5-5 mm (e.g., 2-5 mm, such as 3-5 mm) greater than the lateral width of shaft 26.

For some applications, appendage 28 is self-expanding, and is transitioned into its expanded state by exposing it from sheath 26. For example, appendage 28 can comprise an elastic and/or shape memory material such as Nitinol. For some applications, appendage 28 has a stent structure. For some applications, appendage 28 has a braid structure. For some applications, appendage 28 is mechanically expanded, e.g., using an actuator. For some applications, appendage 28 is expanded using a balloon.

For some applications, one or more imaging techniques (e.g., echocardiographic and/or fluoroscopic guidance) are used to facilitate placement of marker 32 and/or marker 34. For example, although for some applications abutment of appendage 28 against leaflets 14 can be detected via tactile feedback, this can be alternatively or additionally determined using one or more imaging techniques.

A distance d1 can be calculated or measured between the marker 32 at tissue site 42, and marker 34 at tissue site 44. The distance can be measured by observing markers 32 and 42 using fluoroscopy (e.g., determining d1 from measurement of the distance between markers on a fluoroscopy image), and/or by judging the relative insertion distance of tools 22 and 24 (e.g., a proximal end remaining outside the body can include markings or gradations to show relative distance between the tools and their markers when the markers are positioned as desired). It is hypothesized by the inventor that fluoroscopy provides a more accurate indication and/or measurement of distance d1 than do other techniques, such as echocardiography.

Responsively to measured distance d1, an appropriate chord-length is determined for an artificial chord (i.e., an artificial chorda tendinea) or other tether or line to be implanted in the heart. For some applications, the chord/tether-length can be equal to distance d1. For some applications, the chord/tether-length can be greater than distance d1. For some applications, the chord/tether-length can be smaller than distance d1.

An artificial chord 60 or other tether/line (discussion of chord 60 also applies to other tethers/lines that can serve other functions and/or be positioned differently from an artificial chorda tendinea), having the determined chord/tether-length, is subsequently implanted in the heart. For some applications, chord/tether 60 is selected from a selection of chords/tethers that includes at least one chord/tether that does not have the determined chord/tether-length. For some applications, chord/tether 60 is adjusted to the determined chord/tether-length. For some applications, chord/tether 60 is trimmed to the determined chord/tether-length.

Figure 1D:
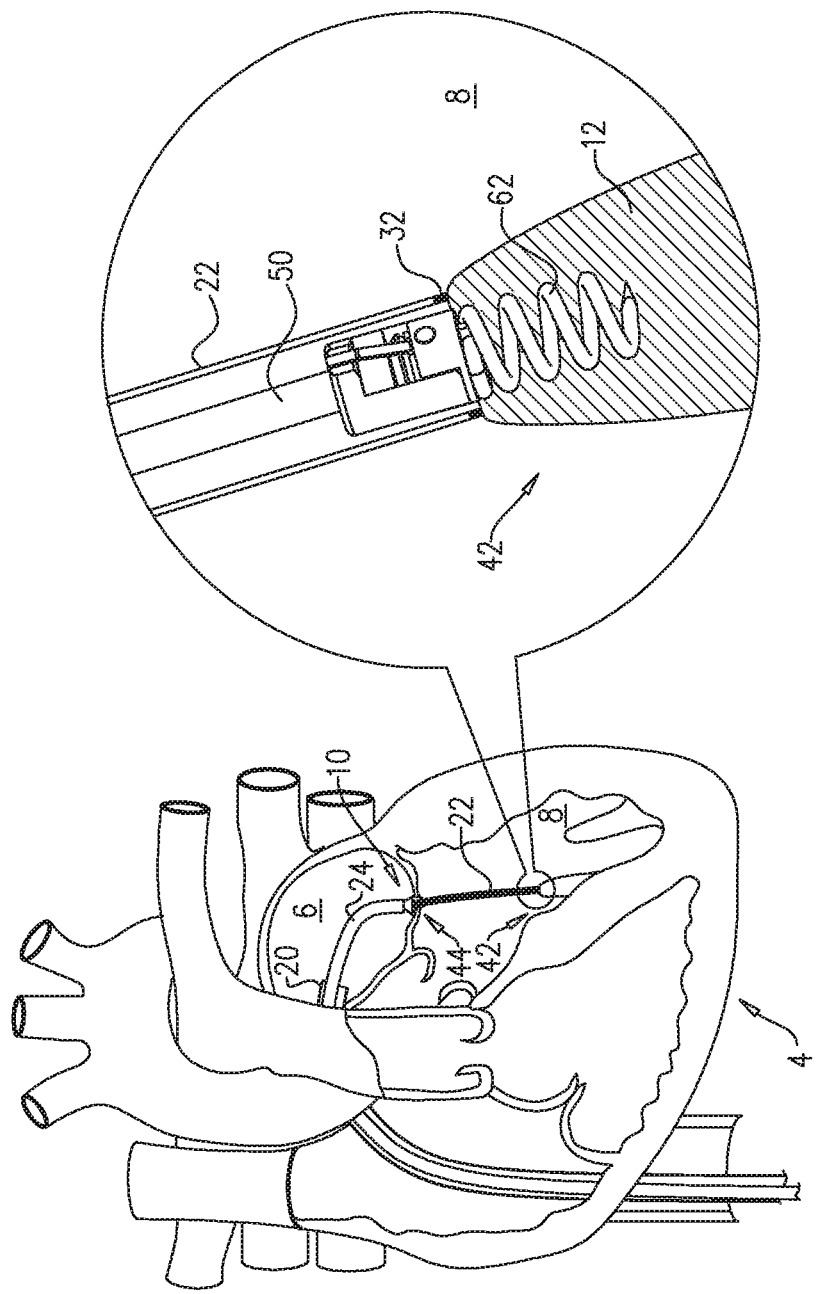
Figure 1E:
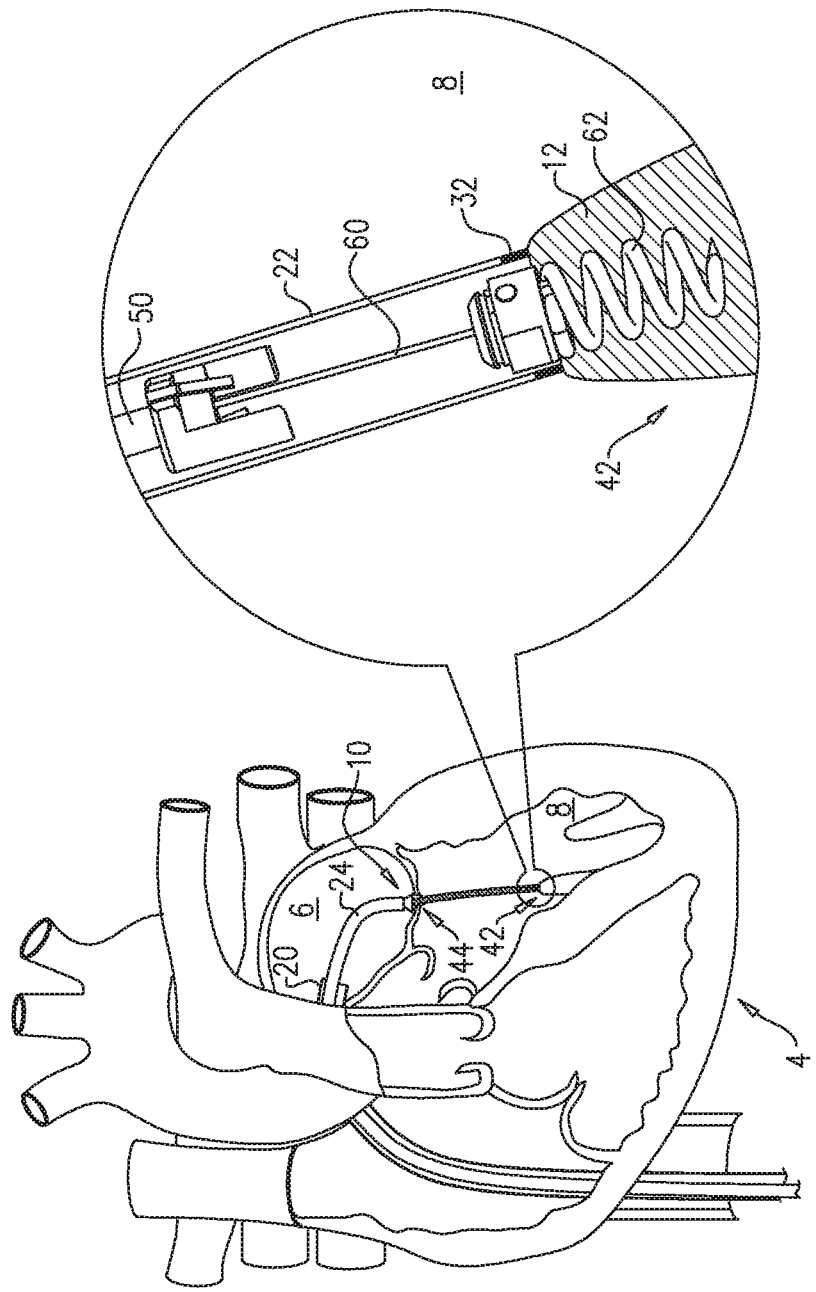
Figure 1F:
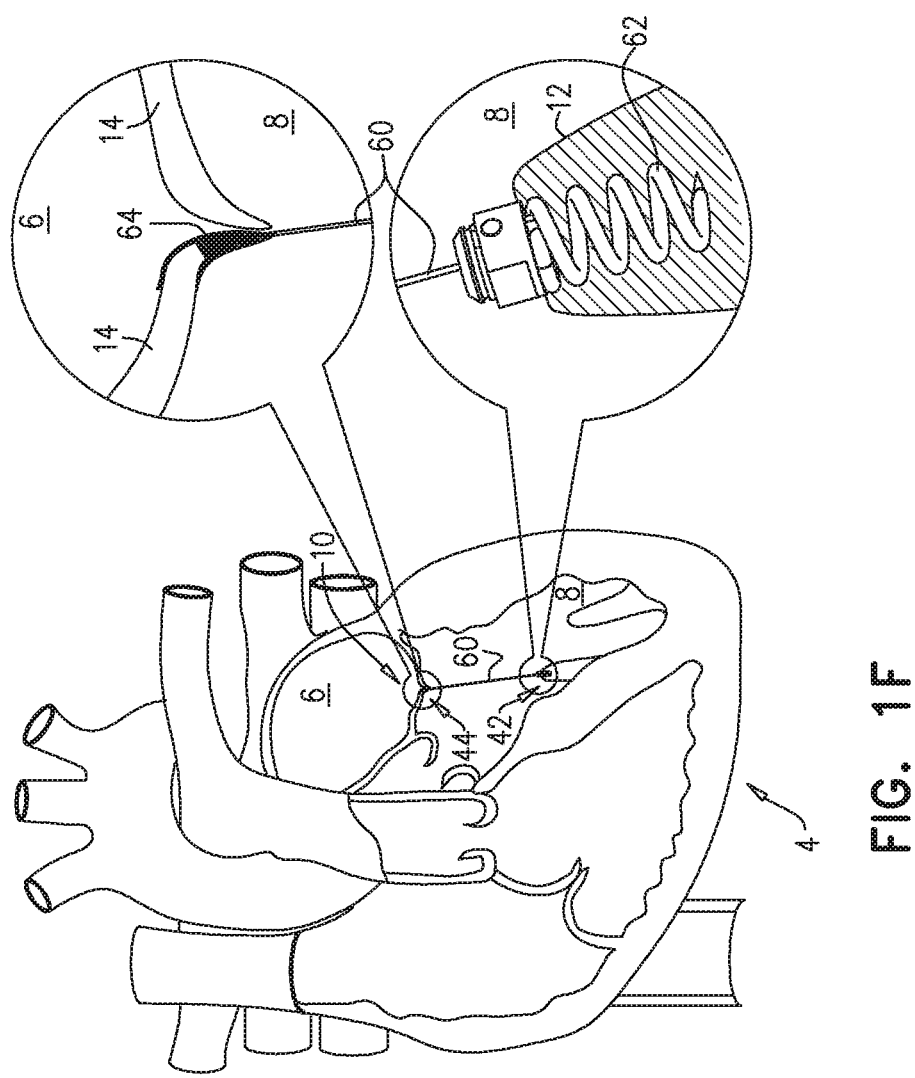

FIGS. 1D-F show implantation of chord/tether 60, in accordance with some applications of the invention. Chord/60 is attached to tissue sites 42 and 44. That is, a first end portion of chord/tether 60 is attached to site 42 (FIG. 1D), and a second end portion of the chord/tether is attached to site 44 (FIG. 1F). These end portions can be attached in a variety of different ways.

For some applications, tool 22 is shaped to define a lumen therethrough, and chord/tether 60 is advanced to the heart within the lumen. For such applications, the attachment of the first end portion of chord/tether 60 to tissue site 42 is typically performed without removing tool 22 from the tissue site. That is, for such applications, tool 22 can remain at the same tissue site 42 as when distance d1 was measured, at least until the first end portion of chord/tether 60 is attached to tissue site 42.

For some applications, and as shown, a tissue anchor 62 is attached to tissue site 42 in order to facilitate attachment of chord/tether 60 to the tissue site. However, other types of attachment means can be used, e.g., clips, sutures, adhesives, knots, pledgets, staples, other anchors, etc.

For some applications in which tissue anchor 62 is used, the first end portion of chord/tether 60 is attached to the tissue anchor (i.e., the chord/tether is provided with the anchor pre-attached), and anchoring the tissue anchor to tissue site 42 anchors the first end portion of chord to the tissue site. FIG. 1E shows tool 50 being withdrawn after anchoring tissue anchor 62 to tissue site 42, with chord/tether 60 extending proximally from the tissue anchor.

FIG. 1F shows the second end-portion of chord/tether 60 having been attached to tissue site 44, or in this example, a leaflet 14. This attachment may be performed before or after the attachment of the first end-portion of chord/tether 60 to tissue site 42. For some applications, and as shown, chord/tether 60 can have a clip 64 pre-attached to the second end-portion of the chord, and clipping the clip to leaflet 14 attaches the second end-portion of the chord/tether to the leaflet. It is to be noted that the attachment of chord/tether 60 to site 44 or leaflet 14 can be implemented alternatively or additionally using other techniques, such as with other attachment means described herein and/or technology described, mutatis mutandis, in one or more of the following publications, which are incorporated herein by reference:

U.S. Pat. No. 8,690,939 to Miller et al.
U.S. Pat. No. 8,734,467 to Miller et al.
U.S. Pat. No. 9,277,994 to Miller et al.

Figure 2A:
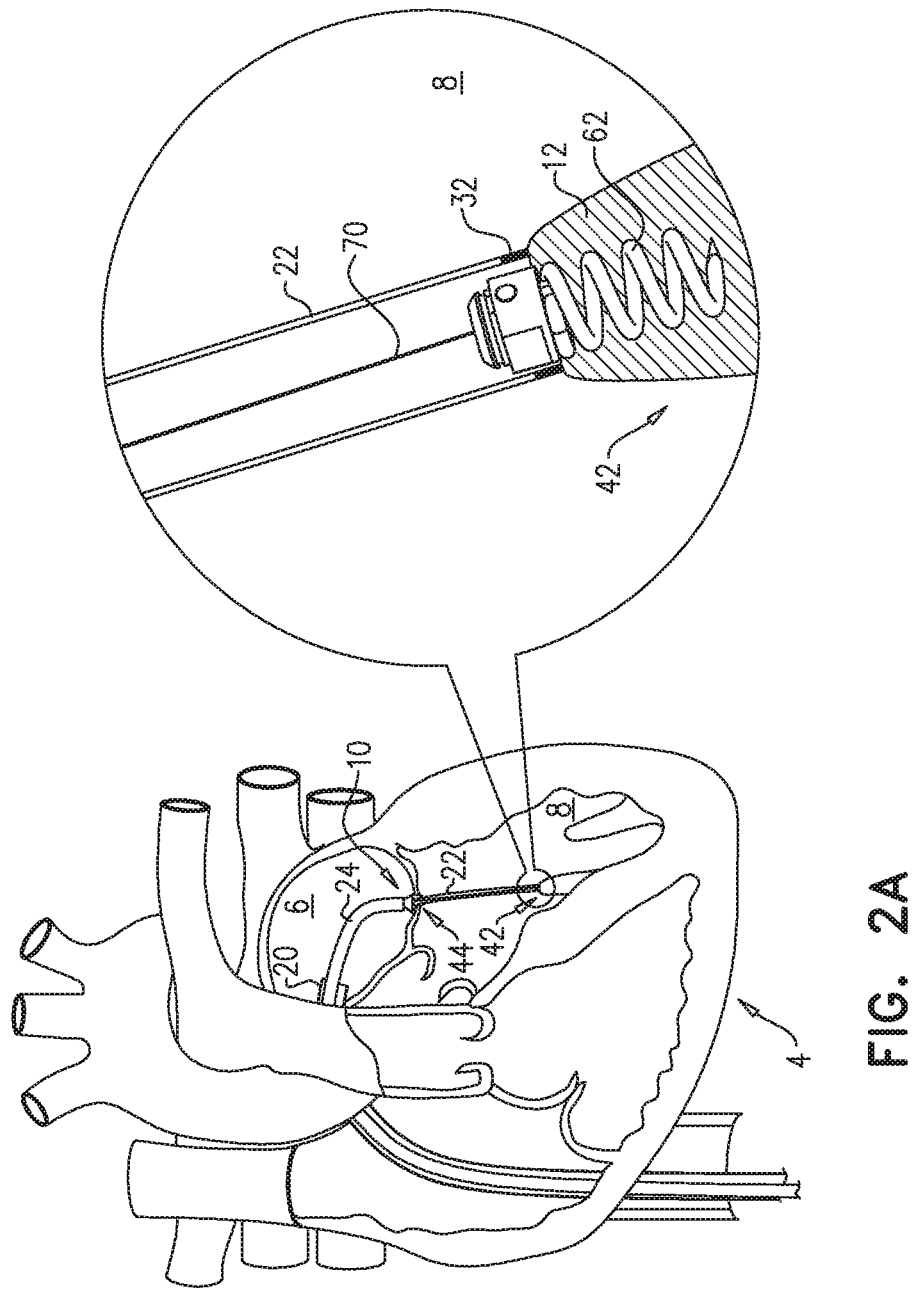
FIGS. 2A-B are schematic illustrations showing an alternative technique for use with the native valve, in accordance with some applications of the invention.
Figure 2B:
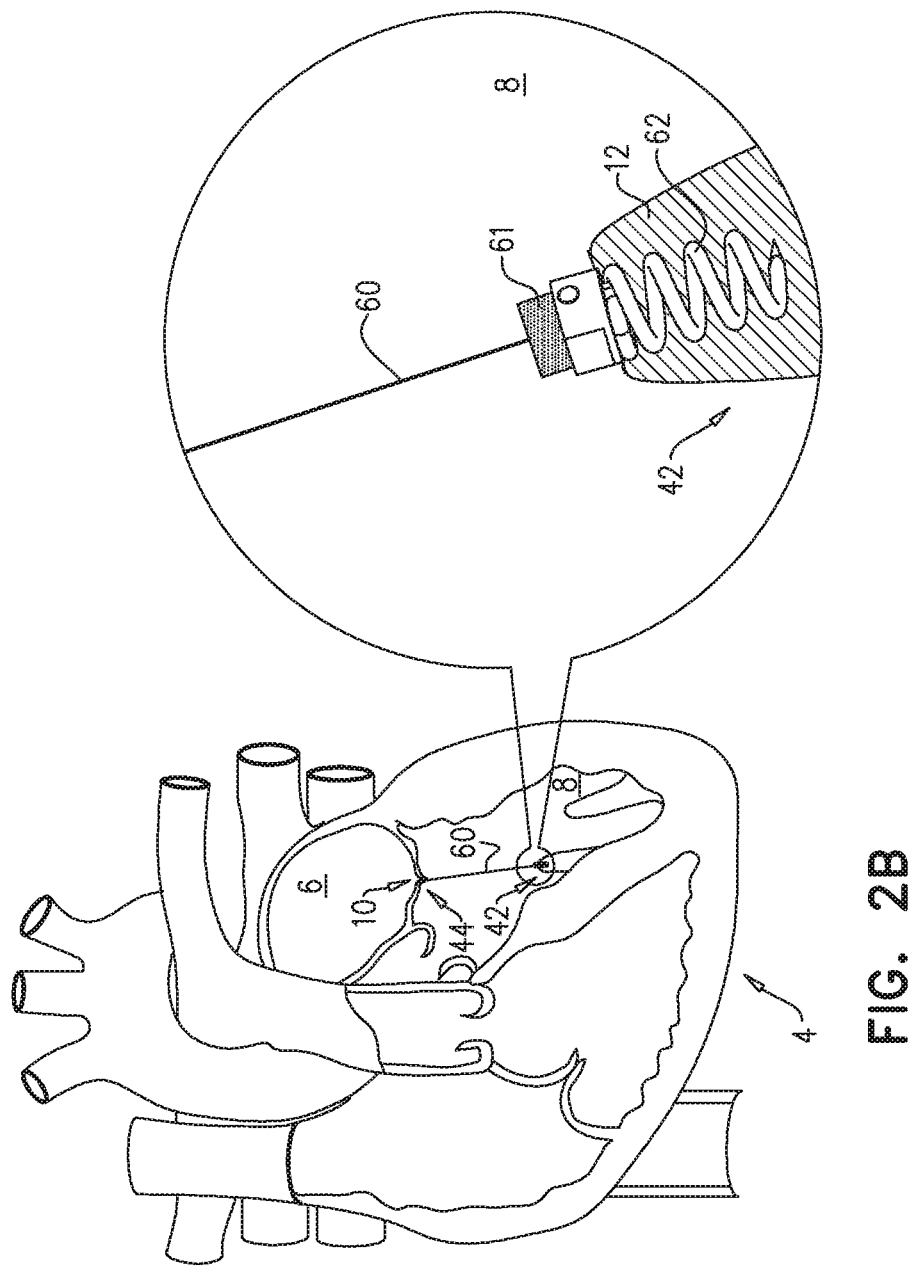

Reference is now made to FIGS. 2A-B, which are schematic illustration showing an optional technique for use with native valve 10, in accordance with some applications. The technique shown in FIGS. 2A-B is typically the same as that of FIGS. 1A-F, mutatis mutandis, except that instead of tissue anchor 62 being provided pre-attached to chord/tether 60, the anchor is coupled to an elongate guide member 70 (i.e., the anchor is implanted with guide member 70 pre-coupled). Anchoring tissue anchor 62 to tissue site 42 anchors guide member 70 to the tissue site. FIG. 2A shows tool 50 having been withdrawn after anchoring tissue anchor 62 to tissue site 42, with guide member 70 extending proximally from the tissue anchor. Subsequently, artificial chord 60 is advanced along guide member 70 (e.g., within tool 22, or after tool 22 has been withdrawn) to tissue anchor 62, and is coupled to the tissue anchor (FIG. 2B). For example, and as shown, a distal end of chord 60 can be attached to a coupling 61 that is configured (e.g., shaped) to lock onto a proximal portion (e.g., a head) of anchor 62. For such applications, guide member 70 is typically subsequently decoupled from anchor 62, and removed from the subject. For some such applications, tool 22 is removed from tissue site 42 (e.g., from the heart entirely) after anchor 62 is anchored, and before chord/tether 60 is advanced along guide member 70 to tissue anchor 62.

For some applications, coupling of chord/tether 60 to tissue anchor 62 can be implemented using attachment means herein or technology described, mutatis mutandis, in one or more of the following publications, which are incorporated herein by reference:

U.S. Pat. No. 8,690,939 to Miller et al.
U.S. Pat. No. 8,734,467 to Miller et al.
U.S. Pat. No. 9,277,994 to Miller et al.

Figure 3:
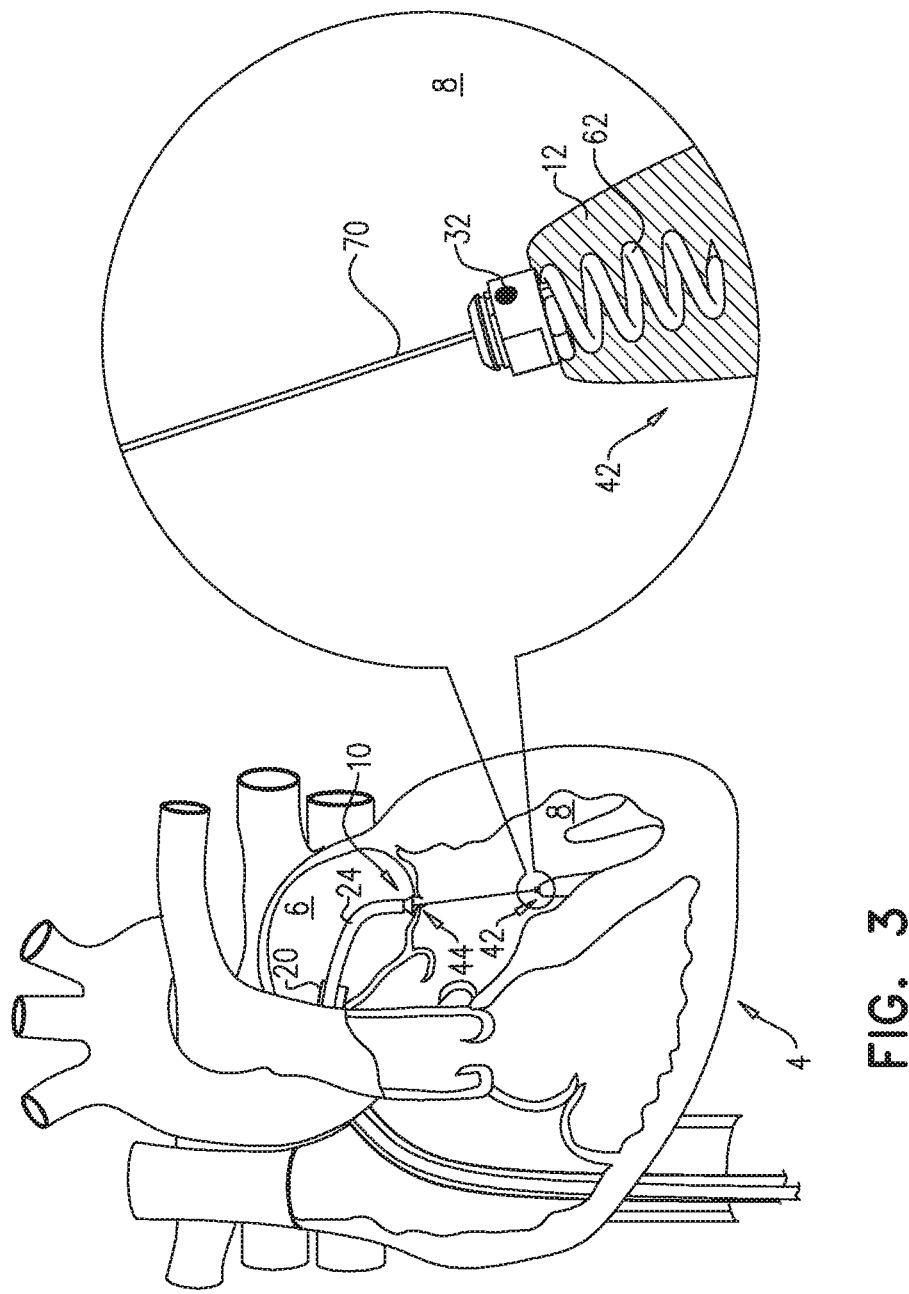
FIG. 3 is a schematic illustration showing another alternative technique for use with the native valve, in accordance with some applications of the invention.

Reference is now made to FIG. 3, which is a schematic illustration showing an optional technique for use with native valve 10, in accordance with some applications. For some applications, tissue anchor 62 comprises or is coupled to first radiopaque marker 32. FIG. 3 shows marker 32 as a distinct component of anchor 62, but it is to be understood that anchor 62 may simply be constructed from a radiopaque material, and thereby serve as marker 32. For such applications, tool 22 may not be used.

FIG. 3 shows the technique described with reference to FIGS. 2A-B having been modified using a radiopaque marker 32 that is a component of or is coupled to anchor 62. The technique described with reference to FIGS. 1A-F can be modified in a similar way, mutatis mutandis. For example, after anchor 62 has been anchored to site 42 (e.g., papillary muscle 12), the distance between markers 32 and 34 is measured, in order to determine the chord/tether-length.

Reference is again made to FIGS. 1A-F, 2A-B, and 3. For some applications, more than one artificial chord or tether is implanted, facilitated by the techniques described hereinabove. For example, a second artificial chord can be attached to a second leaflet 14. For some applications, the second artificial chord can be attached to another ventricular tissue site, e.g., on another papillary muscle or other site. Optionally, the second artificial chord can be attached to the same tissue site 42, e.g., by being attached to the same tissue anchor 62.

Reference is again made to FIGS. 1A-F, 2A-B, and 3. For some applications, the techniques described herein are facilitated by administration of a contrast agent. Although it is hypothesized by the inventor that the techniques described herein provide advantages beyond those provided by contrast agent alone, it is also hypothesized by the inventor that the use of contrast agent may facilitate optimal placement of markers 32 and 34. It is further hypothesized by the inventor that the use of the techniques described herein may advantageously facilitate reduction of the total amount of contrast agent used throughout the procedure.

Reference is again made to FIGS. 1A-F, 2A-B, and 3. The techniques described hereinabove can alternatively or additionally be used with a simulated heart and/or simulated vasculature, e.g., for the purpose of training, and/or for the purpose of planning a procedure on a particular patient. The simulated heart and/or the simulated vasculature may be physical models, e.g., manufactured models, molded models, and/or cadaver models (full cadaver, partial cadaver, and/or cadaver heart), and can be of generalized anatomy or of patient-specific anatomy. Alternatively or additionally, the simulated heart and/or the simulated vasculature can be computer-simulated. With any of these, physical, computer, etc., the simulated techniques can be performed using the same apparatuses, devices, and/or systems as would be used for treating a real subject, mutatis mutandis. Monitors can be used to visualize the procedure and information related to the procedure, e.g., with computers or processors providing input to cause the monitors to display the relevant images and information.

Components, aspects, features, etc. of the systems, apparatuses, devices, methods, etc. described herein can be implemented in hardware, software, or a combination of both. Where components, aspects, features, etc. of the systems, devices, methods, etc. described herein are implemented in software, the software can be stored in an executable format on one or more non-transitory machine-readable mediums. Further, the software and related steps of the methods described above can be implemented in software as a set of data and instructions. Information representing the apparatuses, units, systems, and/or methods stored on the machine-readable medium can be used in the process of creating the apparatuses, units, systems, and/or methods described herein. Hardware used to implement the invention can include integrated circuits, microprocessors, FPGAs, digital signal controllers, stream processors, and/or other components.

The present invention is not limited to what has been particularly shown and described hereinabove. Rather, the scope of the present invention includes both combinations and subcombinations of the various features and steps described hereinabove, as well as variations and modifications thereof that are not in the prior art, which would occur to persons skilled in the art upon reading the foregoing description.

The invention claimed is:

1. A method, comprising:
advancing:
an elongate tool on which a first radiopaque marker is disposed, and
a second radiopaque marker
through vasculature to a heart, the heart having a native valve disposed between an atrium and a ventricle;
placing the first radiopaque marker against a tissue site in the ventricle;
placing the second radiopaque marker against a leaflet of the native valve;
measuring a distance between the first radiopaque marker at the tissue site, and the second radiopaque marker at the leaflet;
responsively to the measured distance, determining a chord-length;
without removing the tool from the tissue site, anchoring a tissue anchor that is coupled to an elongate guide member, to the tissue site;
subsequently, for an artificial chord selected based on the chord-length, implanting the artificial chord by:
advancing the artificial chord along the guide member to the tissue anchor,
attaching a first end portion of the artificial chord to the tissue anchor, and
attaching a second end portion of the artificial chord to the leaflet.

2. The method according to claim 1, wherein:
the vasculature is a physical model of vasculature, and the heart is a physical model of a heart; and
the step of advancing comprises advancing the first radiopaque marker and the second radiopaque marker along the physical model of the vasculature to the physical model of the heart.

3. The method according to claim 1, wherein:
the heart is a simulation of a heart of a particular human subject, and
the method is a method for planning a chord-implantation procedure on the particular human subject.

4. The method according to claim 1, wherein:
the tissue anchor includes the first radiopaque marker, and
the step of anchoring comprises anchoring the first radiopaque marker to the tissue site.

5. The method according to claim 1, wherein placing the first radiopaque marker against the tissue site comprises placing the first radiopaque marker against the tissue site under echocardiographic guidance, wherein placing the second radiopaque marker against the leaflet comprises placing the second radiopaque marker against the leaflet under echocardiographic guidance, and wherein measuring the distance comprises measuring the distance using fluoroscopy.

6. The method according to claim 1, wherein the leaflet is a first leaflet, and wherein placing the second radiopaque marker against the leaflet comprises placing the second radiopaque marker at a coaptation level between the first leaflet and a second leaflet of the valve.

7. The method according to claim 1, wherein the tissue site is on a papillary muscle, and wherein placing the first radiopaque marker against the tissue site comprises placing the first radiopaque marker against the papillary muscle.

8. The method according to claim 1, further comprising selecting the artificial chord based on the chord-length from a selection of chords that includes at least one chord that does not have the chord-length, and further comprising adjusting the artificial chord to the chord-length.

9. The method according to claim 1, wherein:
the leaflet is a first leaflet,
the artificial chord is a first artificial chord,
implanting the artificial chord comprises attaching a first end portion of the first artificial chord to the tissue anchor site and attaching a second end portion of the first artificial chord to the first leaflet, and
the method further comprises implanting a second artificial chord by attaching a second end portion of the second artificial chord to a second leaflet of the native valve.

10. The method according to claim 9, wherein implanting the second artificial chord comprises attaching a first end portion of the second artificial chord to a second tissue site in the ventricle.

11. The method according to claim 1, further comprising, subsequently to anchoring the tissue anchor, removing the first tool from the tissue site and the tissue anchor, wherein advancing the artificial chord along the guide member to the tissue anchor comprises advancing the artificial chord along the guide member to the tissue anchor subsequently to removing the first tool from the tissue site and the tissue anchor.

12. A method, comprising:
advancing:
a first radiopaque marker that is disposed on a first elongate tool, and
a second radiopaque marker that is disposed on a second elongate tool that is slidably coupled to the first tool,
through vasculature to a heart, the heart having a native valve disposed between an atrium and a ventricle;
sliding the second tool with respect to the first tool in order to place at least one radiopaque marker selected from the group consisting of:
the first radiopaque marker, against a tissue site in the ventricle, and
the second radiopaque marker, against a leaflet of the native valve;
measuring a distance between the first radiopaque marker at the tissue site, and the second radiopaque marker at the leaflet; and
responsively to the measured distance, determining a chord-length.

13. A method, comprising:
advancing an elongate tool on which a first radiopaque marker is disposed, and
a second radiopaque marker
through vasculature to a simulated heart, the heart having a native valve disposed between an atrium and a ventricle;
placing the first radiopaque marker against a first tissue site in the ventricle;
placing the second radiopaque marker at a second tissue site at or proximate the valve;
measuring a distance between the first radiopaque marker at the first tissue site, and the second radiopaque marker at the second tissue site;
responsively to the measured distance, determining a tether-length;
without removing the first tool from the first tissue site, anchoring a tissue anchor that is coupled to an elongate guide member, to the first tissue site;

subsequently, implanting a tether, the tether selected based on the tether-length, by:
advancing the tether, along the guide member to the tissue anchor,
attaching a first end portion of the tether to the tissue anchor, and
attaching a second end portion of the tether to the second tissue site.

14. A method for use at a heart having a native valve disposed between an atrium and a ventricle, the method comprising:
advancing, through vasculature to the heart:
a first radiopaque marker, and
an elongate tool on which a second radiopaque marker is disposed;
placing the first radiopaque marker against a tissue site in the ventricle;
placing the second radiopaque marker against a leaflet of the native valve;
measuring a distance between the first radiopaque marker at the tissue site, and the second radiopaque marker at the leaflet;
responsively to the measured distance, determining a chord-length;
without removing the first tool from the tissue site, anchoring a tissue anchor that is coupled to the first elongate guide member, to the tissue site;
subsequently, implanting an artificial chord, the artificial chord selected based on the chord-length, by:
advancing the artificial chord, along the guide member to the tissue anchor,
attaching a first end portion of the artificial chord to the tissue anchor, and
attaching a second end portion of the artificial chord to the leaflet.

15. The method according to claim 14, wherein:
the second elongate tool comprises an appendage on which the second radiopaque marker is disposed;
the method further comprises expanding the appendage within the heart; and
the step of placing the second radiopaque marker against the leaflet comprises advancing the second elongate tool such that the appendage abuts the leaflet of the native valve.

16. The method according to claim 15, wherein laterally expanding the appendage comprises using an actuator to mechanically expand the appendage.

17. The method according to claim 15, wherein laterally expanding the appendage comprises laterally expanding the appendage to a span of 6-15 mm.

18. The method according to claim 15, wherein:
the second elongate tool further comprises a longitudinal shaft, and
laterally expanding the appendage comprises exposing appendage from the shaft.

19. The method according to claim 18, wherein:
the shaft has a lateral width of 2-10 mm, and
laterally expanding the appendage comprises laterally expanding the appendage to a span that is 0.5-5 mm greater than the lateral width of the shaft.

20. The method according to claim 19, wherein laterally expanding the appendage comprises laterally expanding the appendage to a span that is at least twice the lateral width of the shaft.

21. The method according to claim 19, wherein laterally expanding the appendage comprises laterally expanding the appendage to a span that is 2-5 mm greater than the lateral width of the shaft.

22. The method according to claim 21, wherein laterally expanding the appendage comprises laterally expanding the appendage to a span that is 3-5 mm greater than the lateral width of the shaft.

* * * * *